United States Patent [19]

McCandlish et al.

[11] 4,418,154

[45] Nov. 29, 1983

[54] CO HYDROGENATION PROCESS USING MOLYBDENUM OXYCARBONITRIDE CATALYST

[75] Inventors: Larry E. McCandlish, Highland Park; Edwin L. Kugler, Summit, both of N.J.

[73] Assignee: Exxon Research and Engineering Co., Florham Park, N.J.

[21] Appl. No.: 373,886

[22] Filed: May 3, 1982

Related U.S. Application Data

[63] Continuation-in-part of Ser. No. 216,542, Dec. 15, 1980, abandoned.

[51] Int. Cl.$^3$ .............................................. C07C 1/04
[52] U.S. Cl. ................................................... 518/714
[58] Field of Search ........................................ 518/714

[56] References Cited

U.S. PATENT DOCUMENTS

| | | | |
|---|---|---|---|
| 3,492,100 | 1/1970 | Roubin et al. | 23/315 |
| 3,872,136 | 3/1975 | Middelhock et al. | 423/371 |
| 4,128,621 | 12/1978 | Homeier | 423/362 |
| 4,163,775 | 8/1979 | Foster et al. | 423/363 |
| 4,239,536 | 12/1980 | Yamamoto et al. | 75/238 |
| 4,271,041 | 6/1981 | Boudart et al. | |

FOREIGN PATENT DOCUMENTS 54-10692  8/1979  Japan.

OTHER PUBLICATIONS

Le Clercq et al., "Preparation of Catalysts II", Elsevier Sci. Publ. 3, 627 (1979).
Boudart et al., "Seventh International Congress on Catalysis," Tokyo, Jul. 3-4 (1980), Preprint A-40.
Bureau of Mines Report of Investigation #6974 (Jul. 1967).
Nature, pp. 1327-1328 (Jun. 1964).

*Primary Examiner*—Howard T. Mars
*Attorney, Agent, or Firm*—Robert J. North

[57] ABSTRACT

A process for synthesizing light paraffinic hydrocarbons particularly $C_2$-$C_5$ in carbon number, from CO and $H_2$ is described utilizing novel face-centered cubic molybdenum oxycarbonitride catalyst.

11 Claims, 3 Drawing Figures

⦿ = metal atom

○ = heteroatom

CO HYDROGENATION PROCESS USING MOLYBDENUM OXYCARBONITRIDE CATALYST

CROSS REFERENCE TO RELATED APPLICATIONS

This application is a continuation-in-part application of Ser. No. 216,542 filed Dec. 15, 1980 now abandoned.

BACKGROUND OF THE INVENTION

1. Field of the Invention

This invention relates to a process for synthesizing light paraffinic hydrocarbons from CO and $H_2$ by contacting mixtures thereof with face-centered cubic molybdenum oxycarbonitride catalyst, having high activity.

2. Brief Description of the Prior Art

CO hydrogenation, including the Fischer-Tropsch synthesis is well-known in the art for producing a broad range of gaseous liquid and solid hydrocarbons including methane ($C_1$) to $C_{20}$ and higher carbon chain numbers. The process usually uses iron-based catalysts promoted with various agents such as potassium carbonate and the like to improve product distribution and selectivity.

New catalysts for the process are constantly being searched for and evaluated in order to improve the selectivity of the process for producing a particular range of hydrocarbons for example, $C_2$–$C_5$, and to stabilize this selectivity over a broad range of operating parameters.

SUMMARY OF THE INVENTION

It has been found that molybdenum oxycarbonitride is an excellent catalyst for use in CO hydrogenation utilizing mixtures of CO and $H_2$, for selectively producing light paraffinic hydrocarbons in high selectivity and activity over a broad range of operating process variables.

The catalyst in the process exhibits high activity at low $H_2$/CO ratios, which means that the catalyst can operate efficiently on carbon monoxide product streams from gasification of refractory carbon as directly produced. Second, the catalyst shows substantial selectivity for producing light paraffinic hydrocarbons, particularly $C_2$–$C_5$ paraffins, which could be used as a clean storable fuel or as a feedstock for steam cracking. Third, this selectivity for $C_2$–$C_5$ products is maintained over a broad reaction temperature range. This stable product distribution with increasing reaction temperature allows higher temperature operations with attendant optimum reaction rates, surprisingly without substantial increases in methane production.

In accordance with this invention there is provided a process for preparing paraffinic hydrocarbons including linear and branched $C_1$–$C_{10}$ carbon chain numbers comprising contacting a gaseous mixture of CO and $H_2$ in a CO/$H_2$ volume ratio of 10:1 to 1:10, respectively, with a catalyst comprised of face-centered cubic molybdenum oxycarbonitride, in which the interstitial oxygen, carbon and nitrogen atoms are distributed throughout the bulk structure, at a temperature of about 100° to 600° C., a pressure of about 0.1 to 100 MPa, and a space velocity of about 100 to 50,000 v/v/hr., and recovering product paraffinic hydrocarbons.

BRIEF DESCRIPTION OF THE FIGURES

FIG. 1 depicts comparative X-ray powder diffraction patterns on the same scale of:

(a) pyrophoric molybdenum oxycarbonitride (under Kapton film) obtained by the thermal decomposition of ethylenediammonium molybdate in a helium atmosphere at about 650° C.; and (b) passivated molybdenum oxycarbonitride, obtained by contacting the pyrophoric form at room temperature with an atmosphere of oxygen/helium. Also illustrated are the peak indices based on the standard cubic unit cell.

Figure 2:
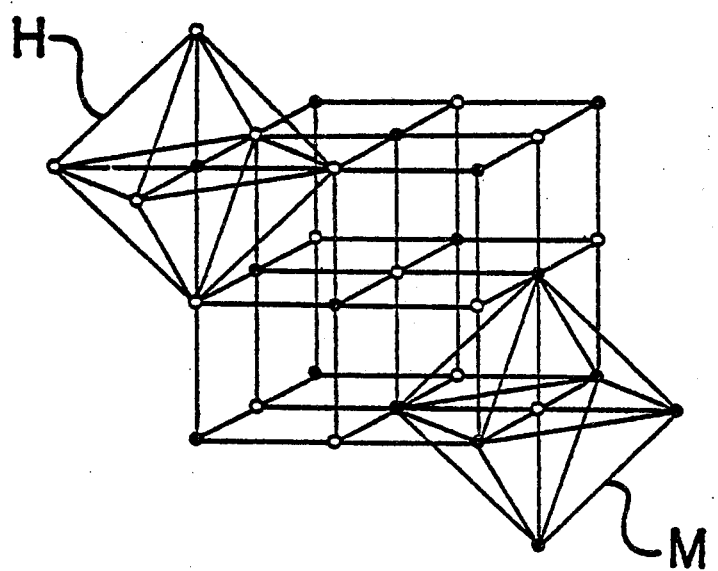

FIG. 2 is a schematic representation of the face-centered cubic molybdenum oxycarbonitride crystal structure, illustrating the metal atom (M) and heteroatom (H) substructures.

Figure 3:
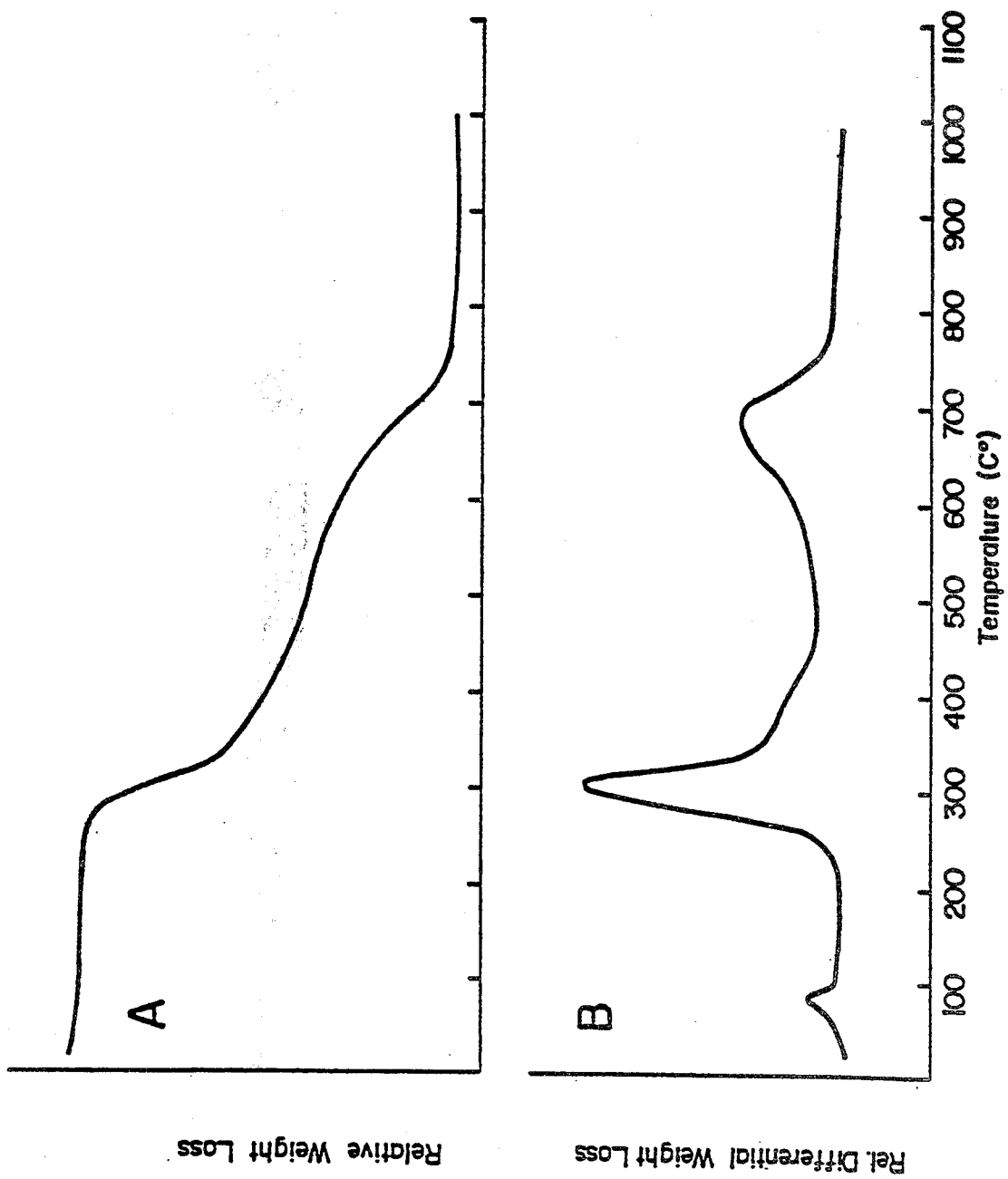

FIG. 3 depicts a thermogram (A) and its derivative (B) illustrating the decomposition of an ethylenediamine adduct of molybdic acid to molybdenum oxycarbonitride as obtained by thermogravimetric analysis.

DESCRIPTION OF THE INVENTION AND PREFERRED EMBODIMENTS

The subject of this invention is a process utilizing said molybdenum oxycarbonitride in producing light paraffinic hydrocarbons from mixtures of CO and $H_2$. Especially noteworthy is the ability of the novel catalyst to selectively produce $C_2$–$C_5$ hydrocarbons under hydrogen-deficient conditions, i.e., greater than 1:3 CO/$H_2$ volume ratios, and to selectively produce this particular hydrocarbon distribution under a wide range of process conditions at high catalyst activities.

The catalyst composition, useful in the process is molybdenum oxycarbonitride which belongs to a general class of materials including interstitial carbides and nitrides which, because of their physical nature, are often not capable of being precisely defined in terms of unique compositional properties as are for example, organic compounds. Interstitial carbides and nitrides, as a class, are generally comprised of two interpenetrating substructures: a metal atom substructure and heteroatom substructure. The metal atom substructure dominates X-ray scattering, predominately determines the X-ray diffraction pattern, and forms a polyhedral array within which the heteroatoms occupy certain positions in the polyhedral interstices, for example, as depicted in FIG. 2. Generally, the metal atom substructure in this class of material differs from the metal atom arrangement in the pure metal, which is usually evidenced by a difference in the X-ray powder diffraction patterns of the materials. However, usually in both cases there is a periodic ordering of the metal atoms. By contrast, the heteroatom substructure may or may not exhibit a periodic ordering and as a further complicating factor, can in general accommodate a varying number of heteroatoms vacancies. Thus, materials in this class of compounds generally exhibit nonstoichiometry with respect to the number of heteroatoms in the interstitial substructure which renders precise definition of the heteroatom substructure very difficult. Further, several different metal atoms substructure arrangements are possible for a given empirical formula. Consequently, this class of materials usually exhibits complex phase diagrams, for example, as is known for molybeenum carbide and tungsten carbide. Thus, precise and complete structural characteriziation of this class of material is a difficult task since the materials, in addition to their nonstoichiometric nature, may also be air-sensitive, pyrophoric, high-melting, and insoluble in standard organic solvents.

With the above discussion as a background, analysis by X-ray diffraction, elemental analysis and thermogravimetric analysis, indicates that the metal atom substructure of molybdenum oxycarbonitride prepared by the process described herein is reasonably believed to be represented as a face cubic-centered lattice as illustrated in FIG. 2. Within the face-centered cubic sturcture of molybdenum oxycarbonitride, as illustrated in FIG. 2, it is believed that each heteroatom site is surrounded by six molybdenum atoms while each molybdenum atom, in turn is surrounded by six heteroatom sites. Thus, the ratio of the number of the heteroatom sites to the number of molybdenum atoms is ideally 1:1. Assuming a random distribution for oxygen, carbon and nitrogen atoms, as well as complete occupancy of all heteratom sites in the heteroatom substructure, leads to the ideal empirical formula for the composition: $MoO_{1/3}C_{1/3}N_{1/3}$. (Amorphous material will vary from this formula due to differences in the number of heteroatom sites as compared to the crystalline structure.) However, since the material can probably support a varying number of heteroatom vacancies within the heteroatom substructure as discussed above, and furthermore, since the ratio of O:C:N atoms, during synthesis would not be expected to be incorporated in exactly a 1:1:1 ratio, it follows that elemental analysis indicates only a general overall heteroatom content and that the ratio of O:C:N will vary to a great extent in the composition.

Within this context, the formula of the novel crystalline composition is $MoO_aC_bN_c$, where a, b and c are non-zero decimal values and the sum: a+b+c, due to nonstoichiometry and difficulty in exact measurement, is less than or equal to about one. (The sum of one being the ideal case under the conditions of exact measurement and complete occupancy of the heteroatom sites.) The ranges for the individual decimal values of a, b and c can vary then, as described above, with the proviso that each individual value is greater than zero and the sum: a+b+c, is not greater than about one for the pure composition.

Figure 1:
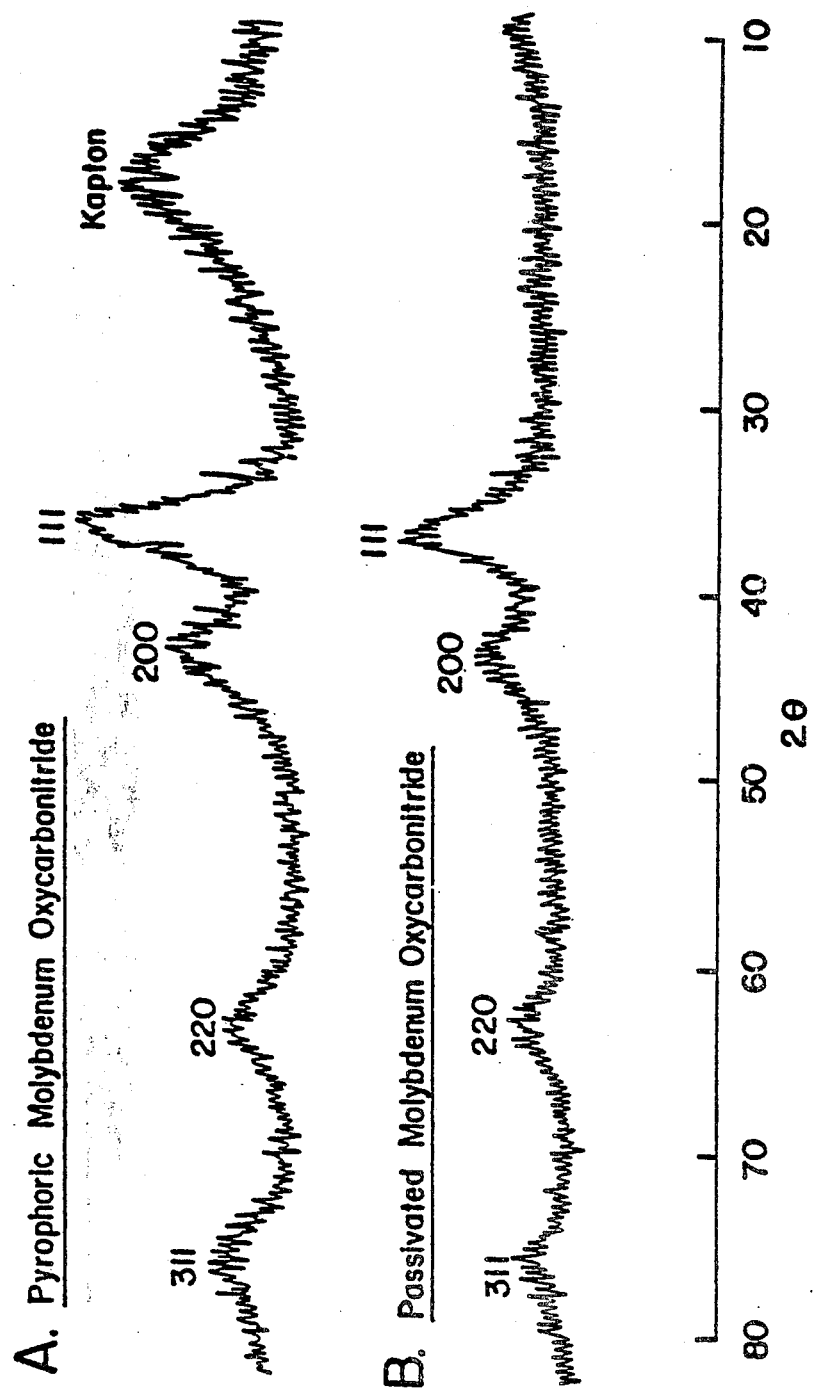

A particular example, described herein, is $MoO_{0.43}C_{0.31}N_{0.33}$, prepared by the decomposition of ethylenediammonium molybdate, whose X-ray diffraction pattern is illustrated in FIG. 1.

Molybdenum oxycarbonitride is generally pyrophoric when freshly prepared by the process described herein and in order to stabilize the material for use as a catalyst, it is usually necessary to passivate it by surface oxidation at room temperature by conventional techniques. For example, the passivating step can be conducted by contacting the pyrophoric material with a stream of oxygen/helium at room temperature in stages of increasing oxygen concentration from about 2 to 10 volume percent or higher to yield, for example, $MoO_{0.99}C_{0.31}N_{0.33}$, whose X-ray diffraction pattern is illustrated in FIG. 1(B).

X-ray diffraction analysis (see FIG. 1) also is consistent with the high surface areas of the obtained composition. Surface areas, as measured by the well-known argon BET method, can be on the order of about 10 to 160 m²/g and higher, preferably 60 to 130 m²/g, and particularly preferred about 100–130 m²/g, and this is evidenced by relatively wide peak half-widths in the X-ray diffraction pattern of FIG. 1(A). Here, a crystallite size of about 30 to 40 Angstroms is inferred from the observed half-widths. Generally, for catalysis, at least 60 m²/g surface areas and higher are generally preferred.

The catalyst composition can exist in amorphous, poorly crystalline, or crystalline forms which can be evidenced by their respective X-ray diffraction patterns.

By the term "amorphous" is meant an X-ray diffraction pattern exhibiting essentially a straight line. By the term "poorly crystalline" is meant an X-ray diffraction pattern exhibiting distinct yet broad scattering peaks, as depicted in FIG. 1(A). By the term "crystalline" is meant X-ray diffraction pattern, exhibiting very sharp scattering peaks. In general, large particle size crystalline materials exhibit narrow diffraction lines and amorphous material exhibit very broad diffraction lines. Further, it is reasonably believed that the amorphous material, when heated or caused to undergo particle size growth, will exhibit the face-centered cubic structure in the final crystalline form.

Molybdenum oxycarbonitride prepared by the process described herein is generally a black powder, having a very high melting point, is extremely insoluble in common organic solvents, is air and water-sensitive, generally has a crystallographic density of about 8.0 to 10.1 g/cm3, and is usually pyrophoric at room temperatures. The lattice parameters exhibited by poorly crystalline molybdenum oxycarbonitride, prepared by the preferred process, is in the range of about 4.1 to 4.4 Angstroms and can be influenced by the particular atmosphere used as described below.

Also described herein is a process for preparing the catalyst composition. Generally, the process comprises thermally decomposing an aminemolybdate at elevated temperature, under a nonoxidizing atmosphere, preferably a reducing atmosphere, wherein said amine contains at least one single bond C—N grouping, and recovering the resulting molybdenum oxycarbonitride.

By the term "molybdate" as used herein is meant molybdates, polyoxomolybdates, including those formed from molybdic acids, oxides and acid anhydrides, of the formulae: $MoO_3 \cdot xH_2O$, $H_2MoO_4$, $H_2Mo_2O_7$, $H_2Mo_3O_{10}$, $H_6Mo_7O_{24}$, $H_4Mo_8O_{26}$ and the like.

By the term "amine molybdate" as used herein, is meant a compound, salt, complex, or adduct formed between the interaction of an amine and respective molybdic acid, oxide or anhydride as described herein.

Amines that are operable in forming the catalyst composition are alkyl amines, alkylenediamines and aromatic amines that preferably contain 1 to 20 carbon atoms and contain at least one single bond C—N grouping. The reason why this structural limitation is necessary in the process is not clear. One theory that we do not wish to be bound by is that the single bond C—N grouping enables both the carbon and nitrogen fragments of the amine to be simultaneously incorporated upon decomposition into the final oxycarbonitride. Thus, pyridine and ammonia are inoperable as the amine components of the amine molybdate in the process, whereas 4-ethyl-aminopyridine and ethylamine are operable amine components.

The alkylamines and alkylenediamines may be linear or branched and may also contain substituents which are inert under the reaction conditions, e.g., alkoxy or halogen. The aromatic amines may also contain substituents on the aromatic ring which are inert under the reaction conditions, e.g., alkoxy or halogen.

Representative examples include ethylenediamine, butylamine, ethylamine, diethylamine, di-n-butylamine, trimethylamine, triethylamine, 1,3-cyclohexane bismethylamine, aniline, 4-ethylaminopyridine and the like, and mixtures thereof. A preferred amine in the process is ethylenediamine.

The amine molybdate is treated in the process by subjecting the compound to a temperature sufficient to cause thermal decomposition. By the term "thermal decomposition" is meant the process of thermal rearrangement of the compound involving usually carbon-carbon, carbon-nitrogen, molybdenum-oxygen and also carbon-hydrogen bondbreaking, thereby resulting in molybdenum oxycarbonitride. Temperatures at which thermal decomposition of the operable amine molybdate occurs depends upon the particular amine molybdate employed and is usually in the range of about 150° to 800° C., preferably about 300° to 700° C., and particularly preferred about 500°–600° C.

The thermal decomposition is conducted under a nonoxidizing atmosphere, which can be inert and/or reducing in nature, preferably reducing, and includes hydrogen, carbon monoxide, helium and the like, and mixtures thereof. In the process there is preferably a substantial absence of elemental oxygen and water at temperatures above 150° C. during thermal decomposition.

It has been found that in the case of ethylenediammonium molybdate, the compound can be thermally decomposed, if desired, in an atmosphere substantially comprising exclusively helium. However, with other amine molybdates an atmosphere containing some hydrogen gas is usually necessary. Preferably, a small amount of hydrogen gas is used to counteract small traces of oxygen or moisture which may be present in the process atmosphere. The process atmosphere preferably contains about 25 to 50 volume percent $H_2$ in admixture with helium or carbon dioxide.

The process atmosphere can be maintained at atmospheric pressure, under reduced pressure, or greater than atmospheric pressure. Preferably the thermal decomposition is conducted at atmospheric pressure. The process atmosphere can be continuous and dynamic as in a constant flowing stream or used in a tube furnace or can be a static atmosphere as present in an autoclave. Preferred is a constant flowing stream of the atmospheric gaseous mixture.

Space velocity of the inert/reducing gas in a flowing, dynamic atmosphere is not critical and can be conveniently conducted in the range of about 100 to 50,000 v/v/hr. What is important is that the flow of gas should be sufficient to sweep away gaseous by-products from the reaction zone and to maintain a sufficiently high concentration of reducing atmosphere in the vicinity of the amine molybdate.

Apparatus for carrying out the thermal decomposition may be any conventional type known to those skilled in the art and include stainless steel and glass tube furnaces, autoclaves, and the like.

The catalyst composition as used in the process also can be unsupported or supported on conventional materials which are inert under the process conditions. Representative examples of suitable supports are alumina, silica, titania and the like. If supported, the catalyst support can be present in conventional amounts.

The process is conducted by contacting a mixture of carbon monoxide and hydrogen with the above-described catalyst in a conventional reactor. Representative types of reactors and apparatus that can be employed are glass and stainless steel reactors that are vertical, horizontal or down-flow types which utilize the catalyst as a fixed bed, fluid bed, slurry and the like.

The catalyst is generally pretreated at an elevated temperature in a reducing atmosphere for a period of time prior to the process. In general, since the catalysts are generally pyrophoric in air, the passivated catalyst is initially charged to the reactor, and converted to the more highly active non-passivated form in situ. For example, passivated material having a surface area of about 98–100 $m^2/g$ (argon) is reasonably believed to be converted to the active catalyst during $H_2$ pretreatment having a surface area of about 130 $m^2/g$. See Example 2. The temperature, atmosphere and time required are conventional in the art. A set of conditions which was found to be effective was pretreatment at 450° C. in a hydrogen atmosphere, at a space velocity of about 10,000 v/v/hr. for a time of about 2 hours. Other sets of conditions will be obvious to one skilled in the art.

The gaseous mixture of CO and $H_2$ is used in a CO/$H_2$ volume ratio of 10:1 to 1:10, respectively, and preferably a 1:3 to 2:1 ratio. Particularly preferred is a 1:1 or CO/$H_2$ volume ratio, for example, as obtained directly from a coal gasification process.

The CO and hydrogen gases used in the process can also be commercially available, for example reagent, technical or industrial purity and can contain small amounts of other gases which are inert under the reaction conditions such as nitrogen, argon or helium, which can also be used as carrier gases in the process.

The temperature of the process is generally conducted in the range of about 100° to 600° C., and preferably about 225°–450° C.

The pressure of the CO/$H_2$ feedstream in the process is generally carried out in the region of about 0.1 to 100 MPa and preferably about 0.1 to 3.0 MPa (1 atmosphere being equivalent to 0.1 MPa).

The space velocity of the CO/$H_2$ feedstream (including carrier gas, if used) in the process is generally carried out in the range of about 100 to 50,000 v/v/hr. and preferably about 1000 to 5000 v/v/hr.

Product hydrocarbons are collected, separated and purified by conventional methods in the art.

The product paraffinic hydrocarbons include linear and branched $C_1$–$C_{10}$ hydrocarbons, preferably being linear, and include methane, ethane, propane, butane, pentane, hexane, heptane, octane, nonane, decane, isooctane, neodecane, isopentane, neopentane and the like. Preferred are $C_2$–$C_5$ in carbon number, being ethane, propane, butane and pentane, and mixtures thereof, as the main products in the process. Methane is also substantially produced in the process.

Yields in the process of paraffinic hydrocarbons can also vary depending upon the exact conditions employed. Yields of combines $C_2$–$C_5$ hydrocarbons can be about 30–70 wt. % of total hydrocarbons and higher. Yields of methane can be about 30–70 wt. % of total hydrocarbon produced also. By the term "mainly comprised" as used herein is meant that about 30–70 wt. % of total hydrocarbons produced are comprised of ethane, propane, butane, pentane, and mixtures thereof.

Percent CO conversions can vary in the process, depending upon the specific conditions employed, and can be in the range of about 20–80% and higher. Higher pressures generally lead to greater % CO conversions.

The following examples are illustrative of the best mode of carrying out the invention as contemplated by us and should not be construed as being limitations on the scope and spirit of the instant invention.

EXAMPLE 1

Preparation of Ethylenediammonium Molybdate 50 g. of molybdic acid, $H_2MoO_4$, and 750 ml. of pure ethylenediamine were refluxed under stirring for about 16 hours. The resulting white-colored solid was collected on a fritted funnel washed with ethanol to remove any unreacted ethylenediamine and then dried in an oven to remove the ethanol. Obtained was a white solid having the following elemental analysis: %N, calculated 12.6, found 13.99; %Mo, calculated 43.2, found 46.9. The above-described preparation was found to be reproducible.

THERMAL DECOMPOSITION

Thermal decomposition of the above-described ethylene-diammonium molybdate was carried out by preheating a glass tube furnace at about 650° C., through which a stream of helium was flowing at 600 ml/min. The above-prepared sample was placed into a quartz boat which was then placed into the tube furnace. The temperature was allowed to equilibrate for about 5 minutes and then the sample was heated to 650° C., under the helium atmosphere, for about 20 minutes to effect the decomposition. Subsequently, the tube was allowed to cool to room temperature, and the tube was then flushed with helium gas for about 15 minutes. Obtained was a black, pyrophoric material which had the approximate composition: $MoO_{0.43}C_{0.31}N_{0.33}$. The pyrophoric material was passivated by contacting the solid at room temperature with a gaseous mixture of oxygen and helium containing increasing concentrations of oxygen according to the following schedule:

| Feedstream | Time |
|---|---|
| 2% $O_2$/He | 1 hour |
| 4% $O_2$/He | 1 hour |
| 6% $O_2$/He | 1 hour |
| 10% $O_2$/He | 1 hour |

The resulting composition had the empirical formula: $MoO_{0.99}C_{0.31}N_{0.33}$ based on results of the chemical analysis: Mo, 79.77%; O, 13.16%; C, 3.05%; N, 3.79%; H, 0.42%. X-ray analysis showed that in the pyrophoric material, the molybdenum atoms form a cubic closest packet array. Thus, the empirical formula $MoO_{0.43}C_{0.31}N_{0.33}$, indicates that all octahedral interstices are occupied by O, C and N atoms, respectively, (0.43+0.31+0.33=1.07). X-ray line broadening techniques revealed that the passivated material had an average particle size of about 30 Angstroms (Å).

Carrying out the thermal decomposition in carbon monoxide, rather than helium, at 650° C., resulted in a material exhibiting the same face-centered cubic lattice, but having a significantly larger lattice constant, being 4.21 Å versus 4.13 Å. The largest lattice constant, 4.32 Å, was obtained using a reducing atmosphere comprising helium/carbon monoxide mixture.

EXAMPLE 2

The following experiments were conducted to illustrate the reversibility of the passivated and surface active crystalline forms of the above-described oxycarbonitride.

A. The passivated material described in Example 1 was treated at 450° C. with a stream of hydrogen for 0.5 hours. The resulting pyrophoric black solid had a surface area of about 135 $m^2/g$ (as measured by standard argon-BET method).

B. The resulting material from A above was passivated by the procedure described in Example 1 resulting in a passivated material having an argon-BET surface area of about 98 $m^2/g$.

C. The resulting material from B above was treated with a stream of $H_2$ at 450° C. for 0.5 hours resulting in a pyrophoric black powder having a BET surface area of about 131 $m^2/g$.

EXAMPLE 3

Ethylenediammonium molybdate prepared as in Example 1 was thermally decomposed in the tube furnace described in Example 1, at 350° C. with a stream of helium (600 ml/min.) for 1.5 hours. The resulting black solid had an argon-BET surface area of about 18 $m^2/g$ and the X-ray diffraction pattern indicated the solid was "amorphous" molybdenum oxycarbonitride.

EXAMPLE 4

Following the general procedure outlined in Example 1, the following amine molybdates, prepared from molybdic acid ($H_2MoO_4$), were thermally decomposed to yield molybdenum oxycarbonitride. Exact conditions used are listed in Table I. Each of the materials was passivated after formation according to the procedure described in Example 1.

TABLE I

| | Amine Molybdate | Temp. | Atmosphere[a] | Time |
|---|---|---|---|---|
| (1) | 1,3-cyclohexane-bis-methylamine | 400° C. | 75/25 $H_2$/He | 20 min. |
| (2) | trimethylamine | 400° C. | 100% $H_2$ | 20 min. |
| (3) | di-n-butylamine | 400° C. | 75/25 $H_2$/He | 20 min. |
| (4) | aniline | 400° C. | 75/25 $H_2$/He | 20 min. |
| (5) | dimethylamine | 400° C. | 50/50 $H_2$/He | 20 min. |
| (6) | ethylamine | 400° C. | 50/50 $H_2$/He | 20 min. |

[a]flow rate of 600 ml/min.

X-ray diffraction analyses indicated that molybdenum oxycarbonitride was formed in each of the above cases.

COMPARATIVE EXAMPLE 1

Ammonium molybdate (commercially available) was thermally treated following the general procedure described in Example 1 in a 1:1 $CO/H_2$ flowing atmosphere at 500° C. Analysis by X-ray diffraction of the obtained solid indicated that it was not molybdenum oxycarbonitride.

COMPARATIVE EXAMPLE 2

A pyridine salt of molybdic acid (prepared by refluxing a mixture of molybdic acid and pyridine) was thermally treated in an argon atmosphere at 400° C. according to the general procedure described in Example 1. Analysis by X-ray diffraction of the obtained solid indicated that it was not molybdenum oxycarbonitride.

EXAMPLE 5

Five tenths cc of passivated molybdenum oxycarbonitride having a measured BET argon surface area of 98-100 $m^2/g$, was placed in a down flow pyrex glass reactor. The catalyst as a fixed bed was pretreated in situ with hydrogen gas at 450° C. for 1 hour at 0.1 MPa and at a space velocity of about 2,400 v/v/hr. Four runs were conducted by passing a stream of CO/H$_2$ in varying volume ratios of from 1:3 to 4:1 at a space velocity of 2,400 v/v/hr. and a pressure of 0.1 MPa, over the catalyst maintained at a temperature of about 299° C. Each run was carried out over a 4 hr. period. The products from each run were analyzed by on-line gas chromatography. Results are indicated below in Table II.

TABLE II

| CO/H$_2$ Ratio | Temp. | % CO Conv.[a] | Rate[b] | Hydrocarbon Products[c] | | | | |
|---|---|---|---|---|---|---|---|---|
| | | | | C$_1$ | C$_2$ | C$_3$ | C$_4$ | C$_5$+ |
| 1:3 | 299° C. | 34.2 | 149.2 | 54 | 31 | 11 | 3 | 1 |
| 1:1 | " | 17.3 | 150.9 | 43 | 34 | 17 | 4 | 2 |
| 2:1 | " | 8.4 | 73.3 | 41 | 37 | 17 | 4 | 1 |
| 4:1 | " | 2.2 | 38.4 | 44 | 42 | 13 | t[d] | t[d] |

[a]Percent CO conversion
[b]Rate of CO conversion in micromoles CO/minute/g of catalyst
[c]Wt. % of total hydrocarbons produced
[d]Trace Quantity As is seen from the above Table, equivalent rates of CO conversion are observed at CO/H$_2$ reactant ratios of 1:3 to 1:1. The rate decreased when the CO/H$_2$ ratio was increased above 1:1. The CO/H$_2$ volume ratio had little effect on the overall hydrocarbon product distribution. Reducing the CO/H$_2$ volume ratio brought only a small decrease in methane and small increase in higher hydrocarbon selectivities, demonstrating the stable product composition with changing reactant gas composition.

EXAMPLE 6

Using the same catalyst, apparatus and general procedure described above in Example 6, a series of runs was conducted to illustrate the influence of temperature on the hydrocarbon product selectivity. Five runs were made at temperatures ranging from 254° to 315° C., at a CO/H$_2$ volume ratio of 1:1, a pressure of 0.1 MPa, and a space velocity of 2,400 v/v/hr. The results are tabulated below in Table III.

TABLE III

| Temp. (°C.) | CO/H$_2$[b] | % CO Conv. | Hydrocarbon Products[a] | | | | |
|---|---|---|---|---|---|---|---|
| | | | C$_1$ | C$_2$ | C$_3$ | C$_4$ | C$_5$+ |
| 315 | 1 | 20.0 | 45 | 34 | 16 | 4 | 1 |
| 299 | 1 | 17.3 | 43 | 34 | 17 | 4 | 2 |
| 282 | 1 | 13.1 | 41 | 34 | 18 | 5 | 2 |
| 265 | 1 | 10.1 | 39 | 33 | 21 | 5 | 2 |
| 254 | 1 | 8.1 | 39 | 33 | 20 | 6 | 2 |

[a]Wt. percent of total hydrocarbons produced
[b]Volume ratio

As is seen, decreasing the process temperature brought about a slight decrease in selectivity to methane. However, the product distribution was not substantially affected by changes in reaction temperature, demonstrating the stability of the product distribution over a wide range of operating temperatures.

EXAMPLE 7

A series of runs were made with the molybdenum oxycarbonitride catalyst described in Example 6 (having about the same surface area) and two commercially available molybdenum catalysts to determine catalyst activity differences as measured by % CO conversion.

Using the general procedure of Example 6, approximately one-half gram samples of the catalysts were charged into a downflow stainless steel reactor and the catalysts were treated in situ with hydrogen gas at 400° C. for 1 hour at 0.1 MPa and at a space velocity of about 9,600 v/v/hr. The catalysts were each then run under substantially the same process conditions at a H$_2$/CO volume ratio of 1, a CO/H$_2$ feedrate of 20 cc/min., a pressure of 1.0 MPa, and a temperature of 300° C. The products from each 4 hour run were analyzed by on-line gas chromatography and the results indicated in the Table below.

TABLE IV

| Catalyst | Catalyst Weight (grams) | % CO Conversion | Hydrocarbon Product Distribution (wt %) | | | | |
|---|---|---|---|---|---|---|---|
| | | | C$_1$ | C$_2$ | C$_3$ | C$_4$ | C$_{15}$ |
| MoO$_x$C$_y$N$_z$ | 0.523 grams | 27.9% | 56.5 | 20.8 | 11.4 | 3.5 | 7.8 |
| Mo$_2$C[a] | 0.531 grams | 3.3% | 44.4 | 31.5 | 15.3 | 6.9 | 1.9 |
| Mo$_2$N + MoN[b] | 0.502 grams | 0.5% | 54.1 | 30.7 | 15.1 | trace | 0 |

[a]Molybdenum carbide from Alfa Products, Danvers, Mass. Lot #040679.
[b]Molybdenum nitride from Alfa Products, Danvers, Mass. Lot #090880.

As is seen from the data, the molybdenum oxycarbonitride catalyst displays a much higher catalyst activity by comparison to the other materials under substantially the same hydrocarbon synthesis process conditions.

What is claimed is:

1. A process for preparing paraffinic hydrocarbons including linear and branched C$_1$–C$_{10}$ carbon chain numbers comprising contacting a gaseous mixture of CO and H$_2$ in a CO/H$_2$ volume ratio of 10:1 to 1:10, respectively, with a catalyst comprised of face-centered cubic molybdenum oxycarbonitride, in which the interstitial oxygen, carbon and nitrogen atoms are distributed throughout the bulk structure, at a temperature of about 100° to 600° C., a pressure of about 0.1 to 100 MPa, and a space velocity of about 100 to 50,000 v/v/hr., and recovering product paraffinic hydrocarbons.

2. The process of claim 1 wherein said molybdenum oxycarbonitride is crystalline and of the formula: MoO$_a$C$_b$N$_c$, wherein a, b and c are non-zero decimal values and wherein the sum of a+b+c is less than or equal to about one.

3. The process of claim 1 wherein said molybdenum oxycarbonitride possess a measured BET argon surface area of about 10 to 160 m$^2$/g.

4. The process of claim 3 wherein said surface area is about 60–130 m$^2$/g.

5. The process of claim 4 wherein said surface area is about 100–130 m$^2$/g.

6. The process of claim 1 wherein said temperature is about 225° to 450° C.

7. The process of claim 1 wherein said pressure is about 0.1 to 3.0 MPa.

8. The process of claim 1 wherein said space velocity is about 1000 to 5000 v/v/hr.

9. The process of claim 1 wherein said CO/H$_2$ volume ratio is about 1:3 to 2:1.

10. The process of claim 1 wherein said product paraffinic hydrocarbons mainly comprise ethane, propane, butane, pentane and mixtures thereof.

11. A process for preparing $C_2$–$C_5$ paraffinic hydrocarbons comprising contacting a gaseous mixture of CO and $H_2$ in a CO/$H_2$ volume ratio of 1:3 to 2:1, respectively, with a catalyst comprised of face-centered cubic molybdenum oxycarbonitride, in which the interstitial oxygen, carbon and nitrogen atoms are distributed throughout the bulk structure, said catalyst having a measured BET argon surface area of about 100–130 $m^2$/g, at a temperature of about 225° to 450° C., a pressure of about 0.1 to 3.0 MPa, and a space velocity of about 1000 to 5000 v/v/hr., and recovering product paraffinic hydrocarbons.